(12) United States Patent
Dutcheshen et al.

(10) Patent No.: US 6,482,770 B2
(45) Date of Patent: Nov. 19, 2002

(54) METHOD AND COMPOSITION FOR PROTECTING PLANTS FROM DISEASE

(75) Inventors: Joseph M. Dutcheshen, Kamsack (CA); Theodore Anthony Danyluk, Melville (CA)

(73) Assignee: Northern Quinoa Corporation, Kamsack (CA)

( * ) Notice: Subject to any disclaimer, the term of this patent is extended or adjusted under 35 U.S.C. 154(b) by 0 days.

(21) Appl. No.: 09/782,696

(22) Filed: Feb. 13, 2001

(65) Prior Publication Data

US 2002/0013229 A1 Jan. 31, 2002

Related U.S. Application Data

(63) Continuation-in-part of application No. 09/504,184, filed on Feb. 15, 2000.

(51) Int. Cl.[7] .......................... A01N 25/26; A01N 27/00
(52) U.S. Cl. ....................................... 504/100; 504/357
(58) Field of Search .............................. 504/100, 104, 504/357

(56) References Cited

U.S. PATENT DOCUMENTS 3,676,102 A * 7/1972 Clark et al. .................. 71/127

FOREIGN PATENT DOCUMENTS

| JP | 07025718 | * | 1/1995 |
| SU | 1729314 | * | 4/1992 |

* cited by examiner

Primary Examiner—Alton Pryor
(74) Attorney, Agent, or Firm—Hovey Williams LLP

(57) ABSTRACT

Improved methods and compositions for protecting plants or seeds from plant diseases are provided. Broadly, the compositions comprise (and preferably consist essentially of) saponin, such as triterpene type saponins extracted from Quinoa or Quillaja. The methods comprise contacting the portion of the plant (e.g., foliage, shoot, etc.) to be treated with a disease-inhibiting or protective amount of the composition. The compositions can also be used to treat plant seeds or tubers prior to planting thereof, as well as soil adjacent a growing plant. The inventive compositions are particularly useful for the treatment, control and/or prevention of fungal diseases. The saponins of the invention can be applied as liquids or dry particulates, and are especially suited for the treatment of potato seed, tubers and plants.

20 Claims, 6 Drawing Sheets

METHOD AND COMPOSITION FOR PROTECTING PLANTS FROM DISEASE

RELATED APPLICATION

This is a continuation-in-part of application Ser. No. 09/504,184, filed Feb. 15, 2000.

BACKGROUND OF THE INVENTION

1. Field of the Invention

The present invention is broadly concerned with methods and compositions for protecting plants from disease. More particularly, the inventive compositions comprise an aqueous solution of saponins. These compositions are directly applied to seeds, seedlings, shoots, foliage, etc. of the plant to be protected. The compositions are particularly useful for protecting the plants against fungal disease.

2. Description of the Prior Art

There are numerous diseases which may harm or even kill plants. Fungal diseases are one such type of disease. For example, *Rhizoctonia solani* (Rhizoctonia Canker, Black Scurf, or *Helminthosporium solani* (Silver Scurf)) and *Phytophthora infestans* (Late Blight) are both fungal diseases which are extremely dangerous to potato crops. In rhizoctonia infections, sclerotia or mycelium invade emerging sprouts, potato stems, roots, and stolons after germination occurring in early spring. On mature tubers or potatoes, the disease appears as black hard bodies known as Black Scurf, with the tuber skin underneath often remaining unharmed. The disease leads to a delay in the emergence of the sprouts and stems, and causes the sprouts and stems to have a reddish canker girdling them when they finally do emerge.

The symptoms of late blight first appear on older leaves soon after flowering of the plant. The leaves turn dark brown and brittle, while the tuber exhibits lesions which often appear around the eyes. Furthermore, the infected portions of the tuber are granular in nature and penetrate as much as 2 cm into the tuber. All of these symptoms cooperate to reduce tuber yields and quality.

Both rhizoctonia and late blight readily infect potato plants and require extreme measures to avoid or minimize transmission thereof. For example, crop rotation is commonly practiced in an attempt to avoid diseased crops. Additionally, growers often seek seeds that are certified as being disease-free. However, these and other currently available measures do not adequately protect against the diseases. There is a need for preventive treatments that will protect potatoes and other plants from these and other harmful diseases.

Quinoa is classified as a member of the Chenopodiaceae, a large and varied family which includes cultivated spinach and sugar beet. Quinoa is an extremely hardy and drought-resistant plant which can be grown under harsh ecological conditions—high altitudes, relatively poor soils, low rainfall, and cold temperatures—that other major cereal grains, such as corn and wheat, cannot tolerate.

Quinoa originated in the Andes region of South America where it was a staple grain in pre-Spanish Conquest times. Traditional uses of quinoa declined after the Spanish Conquest. Cultivation and use of the grain was not widespread until a recent revival due to Western interest in this crop as a high lysine, high protein grain for human consumption. The principal obstacle to even wider human consumption of quinoa has been, and continues to be, the bitter taste of the saponin present in the grain.

Saponins are a type of sterol glycoside widely distributed in quinoa as well as other plants. There are generally two types of saponin—triterpene saponins and steroidal saponins. Traditionally, saponin has been removed by washing the grain in running water, although new methods have been developed recently (see, e.g., WO 99/53933).

Attempts have been made to utilize saponin as a synergist for other compounds which are useful for controlling the growth of pathogens (e.g., fungi) on plants. For example, U.S. Pat. No. 5,639,794 to Emerson et al., is directed towards a method for treating agricultural crops comprising the step of applying a so-called "natural product" in combination with at least one saponin to kill, retard growth of; or displace pathogenic organisms. The natural products combined with the saponin are the various aldehydes, and particularly aromatic aldehydes, and the saponins are used to enhance the activity of the aldehyde (i.e., as a synergist). However, the use of aldehydes increases the cost of treating the plants and, in many instances, may be undesirable to the grower due to environmental concerns as well as the extra effort involved in handling these aldehydes.

There is a need for a cost-effective, environmentally friendly composition for effectively treating and/or preventing diseases in plants.

SUMMARY OF THE INVENTION

The instant invention overcomes the problems of the prior art by broadly providing effective compositions and methods for treating and/or protecting plants from diseases.

In more detail, the inventive compositions comprise (and preferably consist essentially of) saponins which act as a protectant for the plant independent of other compounds or agents (i.e., saponin is the principal and/or only active ingredient). As used herein, "plant" is intended to refer to any part of a plant (e.g., roots, foliage, shoot) as well as trees, shrubbery, flowers, and grasses. "Seed" is intended to include seeds, tubers, tuber pieces, bulbs, etc., or parts thereof from which a plant is grown.

While any saponin is suitable for use in the compositions, the saponin should be derived from a plant different than the plant that the final saponin composition is intended to protect. Suitable sources of saponins include Quinoa, Quillaja, Primula (Primulae sp.), Senega (*Polygala senega*), Gypsophila, Horse chestnut (Aesculus .p.), Ginseng (Panax sp. and Eleutherocosus sp.), Licorice (Glycyrrhiza sp.), Ivy (Hedera sp.), Tea seed (*Camellia cinensis*), Alfalfa (*Medicago sativa*), Soya, Yucca (Yucca sp.), and Dioscorea. It is particularly preferred that the saponin be of the triterpene variety as found in Quinoa and Quillaja versus the steroidal types found in Yucca.

A preferred method of extracting saponins from quinoa comprises placing a saponin-containing portion of a quinoa plant in an aqueous alcohol (e.g., methanol, ethanol) solution to form a saponin-containing solution and an extracted, solid residue. The alcohol is then removed from the solution followed by evaporation of the water to yield the saponin-containing product. Those skilled in the art will appreciate that the saponins can also be extracted from quinoa by other methods for use in the instant invention.

The saponin extract is preferably mixed with water to form the protective composition. If desired, the saponin extract can be mixed with water under mild heat: (e.g., from about 10–35° C.) in order to effect mixing. Alternately, the saponin extract can be applied as a dry composition alone, or blended with a suitable carrier. Preferably, the composition comprises from about 25–300 g of saponin extract, and more preferably from about 50–200 g of saponin extract, per 100 liters of water, where the saponin extract has a triterpene saponin concentration of from about 10–70% by weight, and preferably at least about 50% by weight, based upon the total weight of the saponin extract taken as 100% by weight. Alternately, the saponins of the invention can be applied in a dry formulation using talc or some other particulate carrier. In such cases, the saponin component should be present at a level of from about 8–46% by weight, more preferably from about 16–36% by weight.

In use, plants or seeds are treated with the inventive compositions by simply contacting one or more portions of a diseased plant or seed, or a plant or seed susceptible to attack by disease, with a disease-inhibiting or protective amount of the composition so as to elicit a protective response in the plant or seed. This can be accomplished by spraying the plant or seed as well as by submerging it in the aqueous composition. Those skilled in the art will appreciate that portions of a plant can be selectively treated (e.g., infected leaves can be treated individually or the roots alone can be treated). Additionally, the seeds or tubers can be submerged in the aqueous composition and then planted and allowed to grow into a protected plant. Furthermore, the soil around the plant or seed can be treated as well. When the plant to be treated is a tree, the composition is preferably introduced into the vascular system of the tree by conventional methods. In a similar way, the dry saponin compositions can be applied by dusting or coating a plant part or seed.

It has also been found that the saponin products of the invention, and particularly the liquid versions thereof, are effective as foliar sprays. Such sprays would normally contain concentrations of saponin of from about 1 g/10 L to 150 g/10 L, and more preferably from about 10 g/10 L to 100 g/10 L.

Preferably, the plant or seed is not pre-treated with some other type of pathogen-controlling agent. Furthermore, it is preferred that the plant or seed is not treated with another pathogen-controlling agent simultaneous to treatment with the inventive composition. More specifically, it is preferred that the plants, seeds, or soils surrounding the plants have not been treated with some type of aldehyde composition. Thus, the plant and plant surfaces or the seed and seed surfaces should be essentially aldehyde-free (e.g., less than about 1 mg of aldehyde groups, per square centimeter of plant surface area to be treated) prior to treatment according to the invention.

Virtually any plant can be treated to prevent or lessen most plant diseases. For example, potato plants, sugar beets, canola, strawberries, chick peas, lentils, broccoli, cabbage, cauliflower, turf grass, tobacco, spinach, carrots, ginseng, radish, and field peas or seeds of any of the foregoing can all be protected with the inventive compositions. Furthermore, the compositions can be used to treat, control and/or prevent fugal diseases (e.g., rhizoctonia, late blight), Aphanomyces, Cercospora, Rhizopus, Sclerotium, ergot, Ascochyta, Fusarium, Anthracnose, Botrytis, and Ophiostoma (ceratocystis) ulmi (Dutch Elm disease). Plants or seeds treated according to the invention will remain essentially free of symptoms of the disease for at least about 20 days, preferably at least about 60 days, and more preferably at least about 100 days, after treatment. Thus, plants treated according to the invention, or plants grown from seeds treated according to the invention, will at least exhibit reduced levels of the disease compared to nontreated crops, and preferably will remain essentially free of symptom of the disease throughout the natural growing season of the plant.

DETAILED DESCRIPTION OF THE PREFERRED EMBODIMENTS

Figure 1:
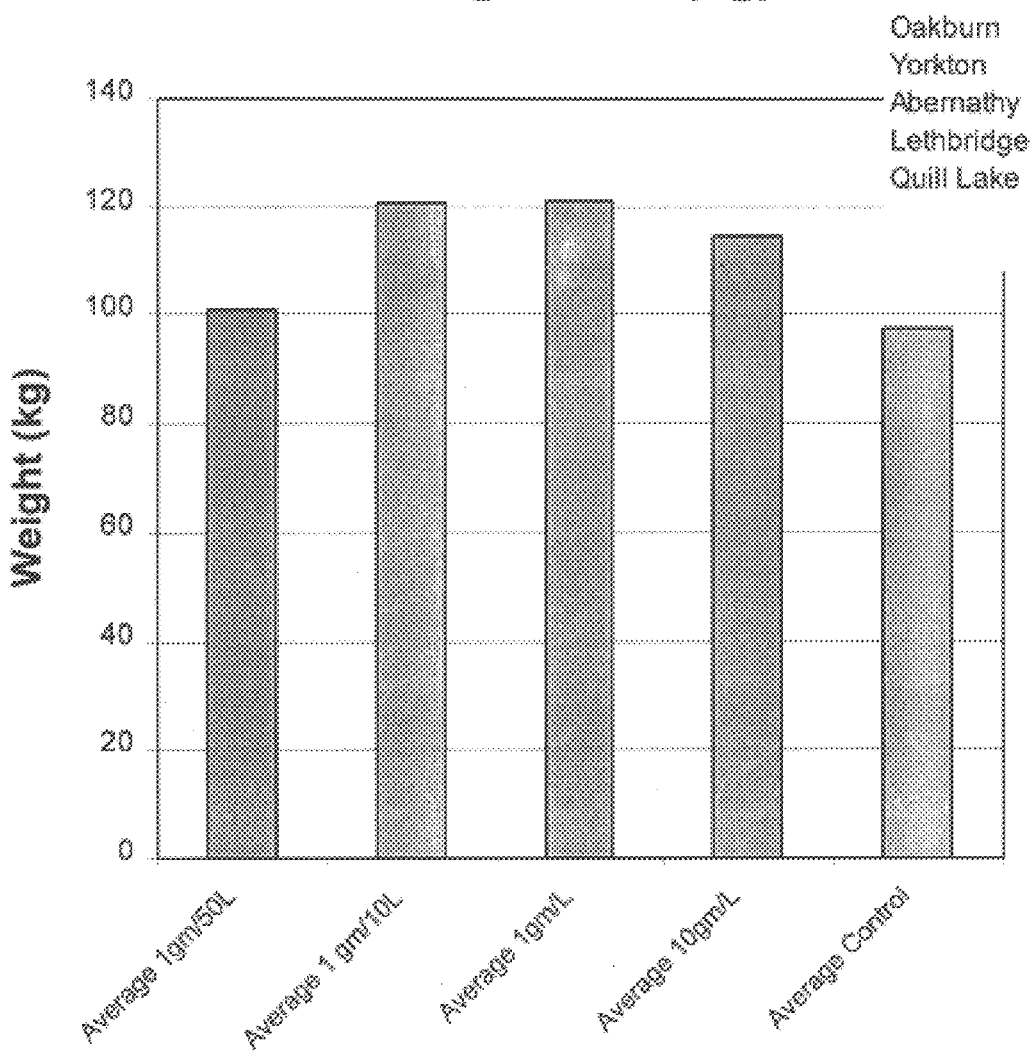
FIG. 1 is a graph illustrating average potato yield data for five test locations wherein potato seed was coated with the saponin products of the invention versus a non-treated control, as described in Example 2.

The following examples set forth preferred methods in accordance with the invention. It is to be understood, however, that this example is provided by way of illustration and nothing therein should be taken as a limitation upon the overall scope of the invention.

EXAMPLE 1

A quantity of the inventive composition was prepared by mixing 250 g of saponin extracted from quinoa with 200 liters of water. Fourth and fifth generation potato seeds were submerged in the solution after which the treated plants were planted along with untreated plants as the control. The quantity of treatment used was 125 g of saponin per acre of planted potatoes. The potato varieties tested were AC Ptarmigan, Norland, Nordonna, Yukon Gold, and Frontier Russet.

Portions of the potatoes were harvested 14 days, 28 days, and 49 days after top kill. The potatoes harvested 14 and 28 days after top kill exhibited no black scurf while 2% of the tubers harvested 49 days after top kill had black scurf. The treated tubers showed an increased yield of 42% above that of the control tubers. Furthermore, only 11% of the treated tubers weighed less than 4 ounces in size while 27% of the control tubers were less than 4 ounces in size. Finally, the control tubers exhibited visible signs of Rhizoctonia on one in three plants while the treated plants showed no signs of the disease until natural attrition or senescence of the plants. The treated plants exhibited vigorous, healthy growth.

EXAMPLE 2

In this example, Norland potato seed pieces were treated with the preferred saponin material in accordance with the invention at five Canadian sites (Yorkton, Sk., Oakburn, Mb., Abernathy, Sk., and Quill Lake, Sk., and Lethbridge, Ab.) in order to determine the efficacy of the treatment for control of diseases during the growing season, and on crop produced. Stand establishment, disease development during the growing season, final yield, marketable yield and disease levels on harvested crop were measured.

In particular, at each location a total of five treatments were carried out, namely a no-treatment control and four coating treatments using different levels of a saponin product. This product was alcohol-extracted saponins from Quinoa dried to a solid residue as described above, and then mixed with water under mild heat to give treatment dispersions of various concentration. This product is referred to as "94815" and contains more than three saponin active components (sapogenins); the three major active ingredients are oleanolic acid, hederagenin and phytolaccinic acid, or analogs thereof.

In particular, the treatments were: 0.02 g/L (treatment #1); 0.1 g/L (treatment #2); 1 g/L (treatment #3); 10 g/L (treatment #4); and no-treatment control (treatment #5). Before coating, the trial seed pieces were suburized (the pieces were cut and allowed to heal) at Yorkton and Lethbridge, while at the remaining locations the treatment was carried out immediately after cutting (no suburization). Thereupon, the seed pieces were simply dip-coated in the respective test dispersions.

In each case, there were eight replications of the five treatments, using eight meter row lengths with common guard rows and two meter spacing between ends of blocks. The following randomized block design was used where "g" refers to guard rows, the numbers 1–4 refer to the above treatments and "C" refers to controls. The plot size in each case was 25 m×25 m (⅙ acre).

```
                      Block Design
 Rep 1      Rep 2      Rep 3      Rep 4
g 1 4 C 2 3 g 4 1 2 3 C g 4 3 C 2 1 g 1 3 2 4 C g   8 meter rows
 Rep 5      Rep 6      Rep 7      Rep 8              2 meter space
g 4 2 1 3 C g C 4 1 3 2 g 1 2 4 C 3 g 3 C 4 2 1 g   8 meter rows
```

The test seed pieces were planted 23 cm apart at a depth of 10 cm. At the time of planting, soil and air temperatures were recorded as well as soil type. During the growing season, dates of emergence, rainfall amounts, irrigation applications and the first visual symptoms of Rhizoctonia in each row were recorded. The test plots were maintained weed free and were beetle controlled. Also, other observable diseases affecting plant growth were monitored, as well as Rhizoctonia spores on stems (first appearance) in each row. Stem counts per row were made at 60 days after emergence. Plants on replications 1, 3, 5 and 7 were pulled at 60 days after emergence, and the following were recorded: Stem and cankor on plants, plant yield (tuber count, weight and range), and evidence of black scurf. At 70 days after emergence, a top kill was performed by shredding or spraying the plants with a commercial potato top dessicant, and harvesting took place at 90+ days after emergence. The following were recorded:

total row yield (weight), total marketable yield (weight), number of tubers of uniform shape and those greater than 45 mm, tuber count per row and size distribution (4 categories, less than 45 mm, 45–55 mm, 55–75 mm and over 75 mm) and the number of tubers showing black scurf and the percentage of surface covered.

The following Table 1 sets forth the averaged 90 day yield data from all sites, and FIG. 1 graphically illustrates this data.

Figure 2:
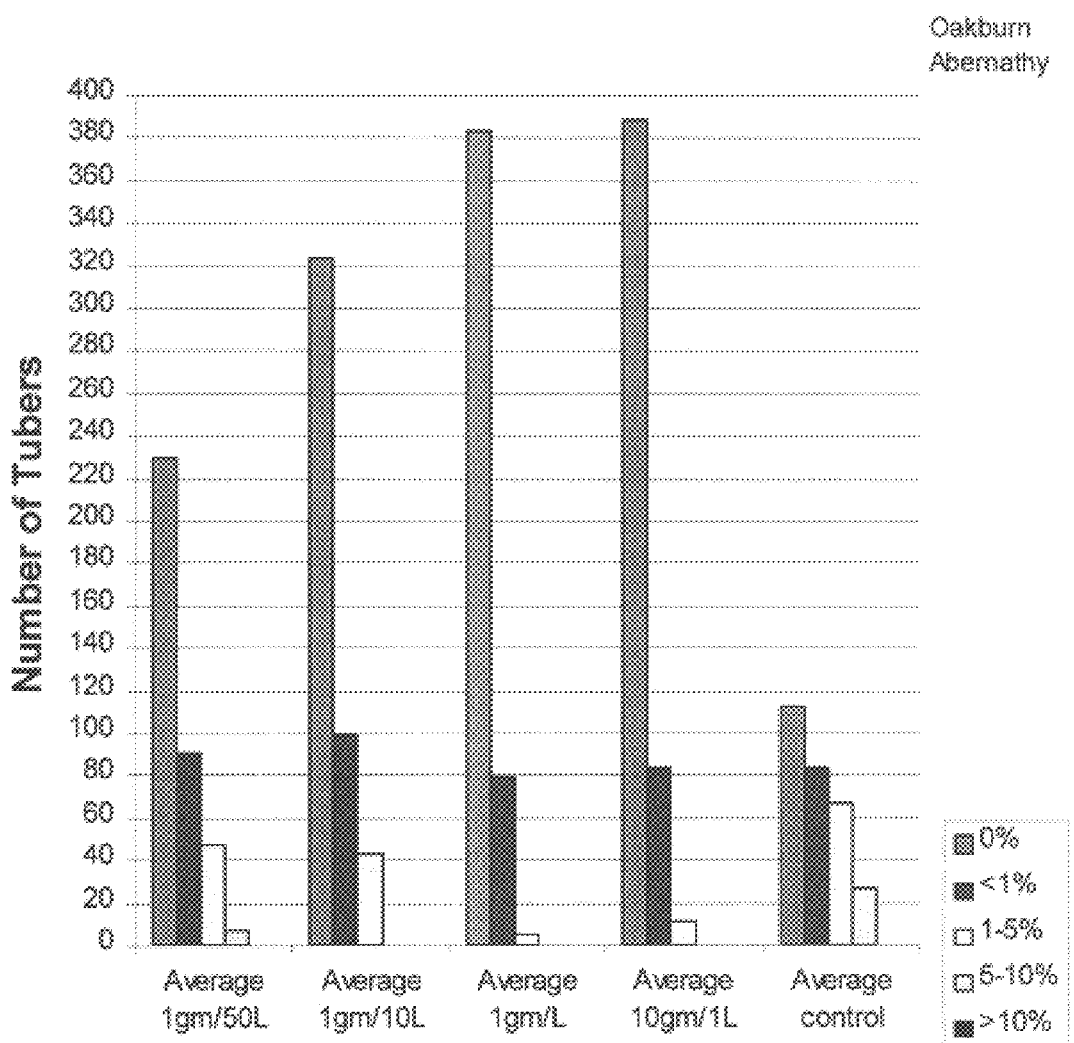
FIG. 2 is a graph illustrating Rhizoctonia level on tubers for two test locations, as described in Example 2.

Table 2 sets forth the Rhizoctonia data for two locations, and FIG. 2 graphically illustrates the data.

TABLE 1

Yield Summary of Five Comparable Locations
Lethbridge must be reviewed on its own because the % count for Rhizoctonia is grouped differently.

| TREAT | PLANTS | TUBERS | WEIGHT |
|---|---|---|---|
| 1: 1 gm/50 L | YIELDS: ALL SITES (kg) | | |
| Oakburn 90 day | 125 | 447 | 61 |
| Yorkton 90 day | 119 | 789 | 111 |
| Abernathy 90 day | 94 | 293 | 61 |
| Lethbridge 90 day | 120 | 1340 | 165 |
| Quill 90 day | 94 | 791 | 108 |
| Average 1 gm/50 L | 110 | 732 | 101 |
| 2: 1 gm/10 L | YIELDS: ALL SITES | | |
| Oakburn 90 day | 131 | 619 | 112 |
| Yorkton 90 day | 127 | 1063 | 138 |
| Abernathy 90 day | 95 | 311 | 65 |
| Lethbridge 90 day | 119 | 1346 | 169 |
| Quill 90 day | 114 | 876 | 120 |
| Average 1 gm/10 L | 117 | 843 | 121 |
| 3: 1 gm/L | YIELDS: ALL SITES | | |
| Oakburn 90 day | 130 | 612 | 116 |
| Yorkton 90 day | 122 | 897 | 127 |
| Abernathy 90 day | 100 | 322 | 81 |
| Lethbridge 90 day | 120 | 1296 | 185 |
| Quill 90 day | 98 | 836 | 117 |
| Average 1 gm/L | 114 | 793 | 121 |
| 3: 10 gm/L | YIELDS: ALL SITES | | |
| Oakburn 90 day | 132 | 607 | 122 |
| Yorkton 90 day | 132 | 932 | 122 |
| Abernathy 90 day | 99 | 362 | 77 |
| Lethbridge 90 day | 118 | 1204 | 144 |
| Quill 90 day | 101 | 863 | 110 |
| Average 10 gm/L | 116 | 794 | 115 |
| Control | YIELDS: ALL SITES | | |
| Oakburn 90 day | 126 | 384 | 54 |
| Yorkton 90 day | 117 | 986 | 134 |
| Abernathy 90 day | 92 | 196 | 31 |
| Lethbridge 90 day | 120 | 1276 | 170 |
| Quill 90 day | 111 | 804 | 99 |
| Average Control | 113 | 729 | 98 |
| SUMMARY | YIELDS: ALL SITES | | |
| Average 1 gm/50 L | 110 | 732 | 101 |
| Average 1 gm/10 L | 117 | 843 | 121 |
| Average 1 gm/L | 114 | 793 | 121 |
| Average 10 gm/L | 116 | 794 | 115 |
| Average Control | 113 | 729 | 98 |
| Average all 94815 | 115 | 790 | 114 |

Yorkton tubers froze in the soil, hence rhizoctonia data not used.
Quill Lake: no rhizoctonia data supplied.

TABLE 2

Oakburn and Abernathy 90 day Tuber Rhizoctonia Summary

| | Number of tubers with Rhizoctonia, 2 locations | | | | |
|---|---|---|---|---|---|
| | 0% | <1% | 1–5% | 5–10% | >10% |
| 1 gm/50 L | | | | | |
| Oakburn 90 day | 248 | 128 | 67 | 14 | 0 |
| Abernathy 90 day | 212 | 54 | 27 | 0 | 0 |
| Average 1 gm/50 L | 230 | 91 | 47 | 7 | 0 |
| 1 gm/10 L | | | | | |
| Oakburn 90 day | 403 | 154 | 61 | 0 | 0 |
| Abernathy 90 day | 244 | 43 | 24 | 0 | 0 |
| Average 1 gm/10 L | 324 | 99 | 43 | 0 | 0 |
| 1 gm/L | | | | | |
| Oakburn 90 day | 514 | 89 | 9 | 0 | 0 |
| Abernathy 90 day | 253 | 68 | 1 | 0 | 0 |
| Average 1 gm/L | 384 | 79 | 5 | 0 | 0 |

TABLE 2-continued

Oakburn and Abernathy 90 day Tuber Rhizoctonia Summary

| | Number of tubers with Rhizoctonia., 2 locations | | | | |
|---|---|---|---|---|---|
| | 0% | <1% | 1–5% | 5–10% | >10% |
| 10 gm/1 L | | | | | |
| Oakburn 90 day | 477 | 113 | 14 | 0 | 0 |
| Abernathy 90 day | 301 | 53 | 8 | 0 | 0 |
| Average 10 gm/1 L | 389 | 83 | 11 | 0 | 0 |
| Control | | | | | |
| Oakburn 90 day | 129 | 118 | 100 | 37 | 0 |
| Abernathy 90 day | 96 | 49 | 34 | 17 | 0 |
| Average control | 113 | 84 | 67 | 27 | 0 |
| Summary | | | | | |
| Average 1 gm/50 L | 230 | 91 | 47 | 7 | 0 |
| Average 1 gm/10 L | 324 | 99 | 43 | 0 | 0 |
| Average 1 gm/L | 384 | 79 | 5 | 0 | 0 |
| Average 10 gm/1 L | 389 | 83 | 11 | 0 | 0 |
| Average control | 113 | 84 | 67 | 27 | 0 |

This example demonstrates the usefulness of the saponins of the invention in preventing and/or minimizing the effects of Rhizoctonia, and further shows that the saponin treatment increases potato yields. Other data confirms that. better results are obtained when the saponin treatment is carried out on freshly cut (non-suburized) seed pieces, or on whole, uncut seed, versus suburized seed pieces.

EXAMPLE 3

In this example, various potato seed piece treatments were compared for their effectiveness in the control of Rhizoctonia, Fusarium and *Helminthosporium solani*. The materials tested are set forth in Table 3, where "Trigger" is a saponin dispersion in accordance with the invention. All products save for the saponin dispersions are commercially available or experimental products designed for control of potato diseases.

METHODS: The test site was located in New Glasgow, Prince Edward Island. Soil type was a sandy loam with a pH of 6.0 and an organic matter content of 2.8%.

The potato seed (Atlantic variety) used in the study had high levels of Rhizoctonia and was also infected with Fusarium by dipping the cutting knives in a slurry of diseased tissue before each cut. Seed was cut by hand on May 17, 2000 and seed treatments were applied on May 18, 2000 by shaking the seed pieces and the appropriate treatment in a plastic tote for two minutes. The saponin dispersion and in-furrow treatments were applied at planting on May 22, 2000. In-furrow treatments were dripped over uncovered seed pieces prior to row closure using a 1 row, hand-held, $CO_2$ sprayer equipped with a drop tube. The saponin dispersion was applied by placing cut seed in the saponin dispersion (10 g dry saponin dispersed in 10 L water) for 30 seconds. After 30 seconds seed was removed from solution and allowed to dry prior to planting. Control treatments received no treatment. Treatments and rates of all products are outlined in Table 3. Each treatment was replicated 4 times in a randomized complete block design. Seed was planted into rows spaced 0.9 m apart with a seed spacing of 35 cm and a depth of 15 cm. Plots were 6 m long and 4 rows wide. 15–15–15 fertilizer was banded during planting at a rate of 775 kg/ha. Insects were controlled with an in-furrow application of Admire (imidacloprid) at 850 ml product/ha at planting. Weeds were controlled with Sencor (metribuzin) at 2.0 kg product/ha on Jun. 4, 2000, and Fusilade II (fluazifop-p-butyl) at 2.0 L product/ha on Jul. 13, 2000. A regular preventative foliar, fungicide program was maintained throughout the growing season. In-season data collected included plant emergence, stem counts, vigor, final stand count, incidence of Fusarium in non-emerged seed pieces, and Rhizoctonia canker on stolons. Plant emergence, stem counts, vigor and final stand count was based on all plants in the two center rows of the plots. Incidence of Fusarium was completed by digging up non-emerged seed pieces in the two center rows. The non-emerged seed piece was identified as being infected by Fusarium, infected with some other pathogen or as a miss (blind seed piece). The percent Rhizoctonia canker rating was taken based on 5 plants per plot. Plots were top-killed on Sep. 10, 2000, using Reglone (diquat) at 2.0 L product/ha and harvested on Oct. 4, 2000. Total and marketable yield was determined at harvest. From the harvested tubers, 10 random tubers per plot were collected for determining the incidence of Silver Scurf (Helminthosporium) and Rhizoctonia after a period in storage. Each 10 tuber sample was placed in a plastic bag with holes punched in it and a wet paper towel was added to each bag to increase the humidity. All samples were stored in the dark until ratings were conducted. Rhizoctonia and Silver Scurf ratings were completed on Nov. 14, 2000. Silver Scurf tuber ratings involved looking at each tuber with a microscope and identifying the fungus as present or not present. Rhizoctonia tuber ratings involved washing the tubers and estimating the percent area covered by the fungus. Data was subjected to analysis of variance and mean separation was conducted where analysis indicated significant differences at the 0.05 level.

RESULTS: No significant differences were seen in emergence or final stand between any of the treatments. Two vigor assessments indicated all the treatments had higher vigor than Trt.#2 (infected check), however, not significantly different. A stem count indicated significant differences between some of the treatments. Trt.#7 (Maxim MZ) had the highest number of stems, while Trt.#9 and Trt.#10 produced the least number of stems. Assessment for incidence of Fusarium on non-emerged seed pieces indicated that no Fusarium was seen in any of the treatments. No significant differences were seen in Rhizoctonia stolon canker, however, Trt.#4 (TM-10%) produced slightly better control. Crop harvest revealed no differences in tuber yield or number of tubers in any size category between any of the treatments. Disease incidence at harvest yielded no significant amounts of late blight or Fusarium. Following approximately 6 weeks in storage Silver Scurf was easily visible on the tuber surface. Results indicated Maxim PSP provided 100% control of Silver Scurf infection, while Maxim MZ provided similar results. Both checks had nearly 50% infection, much higher than most treatments, indicating all treatments provided some control of the fungus. Maxim and Maxim MZ also provided the best control of Rhizoctonia on the tuber surface. All other treatments were not significantly different in their control of Rhizoctonia as compared to the checks. Treatments 3 and 10 did not provide any control of Rhizoctonia, while all other treatments provided some control when compared to the checks, although not significantly different.

CONCLUSION: With the exception of slight differences in stem numbers, no differences between treatments were observed during the growing season or at harvest. Significant differences between the treatments became evident when storage ratings of Rhizoctonia and Helminthosporium were conducted. Maxim PSP and Maxim MZ gave much better control of Helminthosporium and Rhizoctonia on harvested tubers than any other treatment. All other treatments gave some control of Helminthosporium and all treatments except Nos. 9 and 10 provided some control of Rhizoctonia.

This example demonstrates that the saponin product of the invention is at least equivalent to commercially available products. However, the cost of the saponin dispersions is much less than the commercial products. Therefore, effective control can be obtained at less expense and using a preferable natural source product.

TABLE 3

Treatments Used in Study

| Treatment | Product | Application Rate |
|---|---|---|
| 1 | 1 Healthy Check | — |
| 2 | 2 Infected Check | — |
| 3 | 3 PST -- Mancozeb | 10 g/kg seed |
| 4 | 4 TM -- 10% | 5 g/kg seed |
| 5 | 5 TM 2.5% and Mancozeb 6% | 10 g/kg seed |
| 6 | 6 Maxim PSP | 5 kg/kg seed |
| 7 | 7 Maxim MZ | 5 g/kg seed |
| 8 | 8 Trigger liquid seed treatment | dipped in 1 g saponin/L H$_2$O |
| 9 | 9 Treatment No. 9 | 50 ml/100 m2 |
| 10 | 10 Treatment No. 10 | 50 ml/100 m2<br>10 g/kg seed |

Treatment Nos. 9 and 10 are experimental potato treatment agents.

EXAMPLE 4

In this example, potato seed pieces were treated with various compositions to determine the effect thereof upon the control of late blight. The following Tables 4 and 5 set forth the treatment protocol and the coating compositions, respectively.

TABLE 4

Series 2000, Late Blight Seed Treatment
Prosper, ND Non-Irrigated Trials, 2000

| | |
|---|---|
| Plot Design: | 2 × 25 ft. rows; 4 replications/treatment, RCBD. |
| Planting Date: | May 25, 2000 |
| Row Width: | 38 inches. |
| Plant Spacing: | 12 inches. |
| Cultivar: | Norvalley |
| Fertilizer: | 250# 24-12-5 banded at planting. |
| Herbicide: | Treflan (previous fall) |
| | Poast @ 1.5 pt/a on July 10, 2000 |
| | Matrix @ 1.5 oz./a on July 10, 2000 |
| Insecticide: | Admire @ 18 oz./a banded at planting |
| | Asana @ 6 oz./a broadcast on July 10, 2000 |
| Inoculation Method: | Late Blight: For trials 2002–2008 inclusive, 200 fresh cut seed pieces were tumbled with 7 infected seed pieces, infected pieces were then removed and |

TABLE 4-continued

Series 2000, Late Blight Seed Treatment
Prosper, ND Non-Irrigated Trials, 2000

| | |
|---|---|
| | seed was immediately planted; for trials 2001 and 2009–2011, inclusive, induced airborne infection by planting infected plants adjacent the trials. |
| Early Blight: | Natural infection |
| Fungicide Application Dates: | July 9, July 13, July 20, July 27, August 3, August 10, August 18, August 24 |
| Vine-kill: | August 30, 2000, rotobeat. |
| Harvest: | September 16, 2000. |
| Grade: | September 18, 2000. |

NOTE:
Due to heavy rain on June 19, 2000 replications I and II were destroyed.

TABLE 5

Late Blight Seed Treatment Prosper (2000 Series)

| Acc. # | Treatment | Rate | NOTES |
|---|---|---|---|
| 2001 | Uninoculated, UNTREATED | — | |
| 2002 | Inoculated, UNTREATED | — | |
| 2003 | Inoculated, Fungicide #1 | 12 oz/cwt | |
| 2004 | Inoculated, Fungicide #1 | 8 oz/cwt | |
| 2005 | Inoculated, Fungicide #2 | 8 oz/cwt | |
| 2006 | Inoculated, Fungicide #3 | 8 oz/cwt | |
| 2007 | Inoculated, Fungicide #4 | 8 oz/cwt | |
| 2008 | Inoculated, Fungicide #5 | 16 oz/cwt | |
| 2009 | Uninoculated, Trigger (60 sec dip) | 1 g/L | no foliar fungicide |
| 2010 | Uninoculated, Trigger (60 sec dip) | 1 g/L | Bravo or MZ foliar, full season |
| 2011 | Uninoculated, Trigger (60 sec dip) | 2 g/L | no foliar fungicide |

Variety: Norvalley
Planted: 5/25/2000

The "Trigger" products were saponin dispersions in accordance with the invention; all other products were experimental fungicides.

Test results demonstrated that use of the "Trigger" products gave a beneficial effect in controlling late blight, and it is believed that the product will have substantial utility in this context, particularly when used in conjunction with foliar applications through the growth period.

Figure 3:
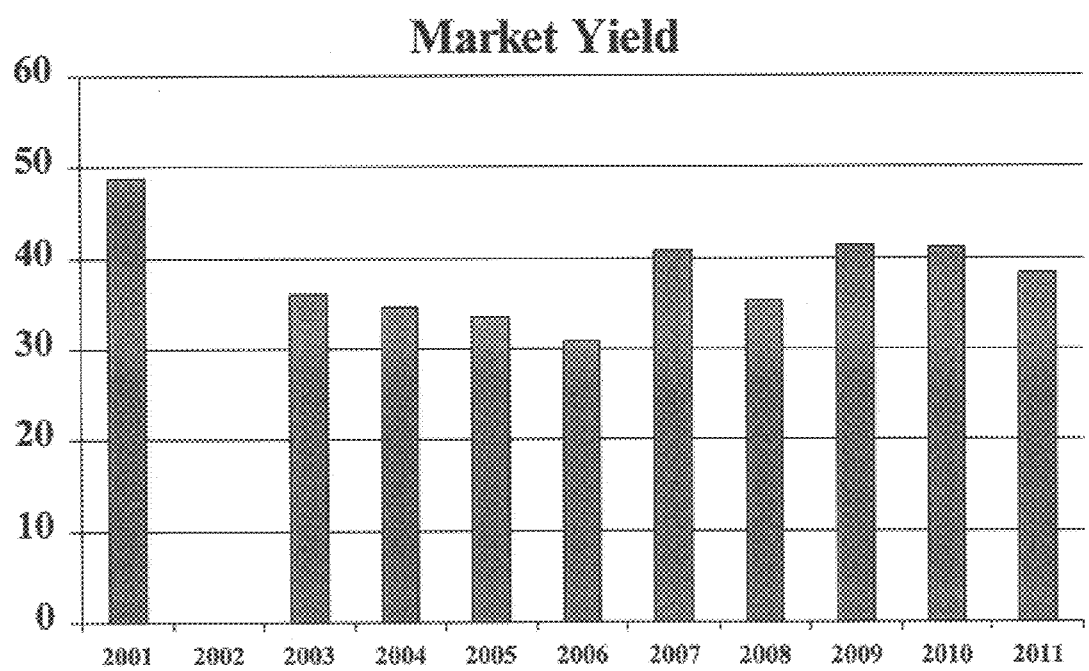
FIG. 3 is a graph illustrating market yields obtained for various test compositions including the saponins of the invention in the late blight test described in Example 4.

FIG. 3 is a graph depicting the marketable yields for the various treatments. It should be noted that the yield using Treatment #2009 was slightly greater than that using Treatment #2010. However, given the fact that Treatment #2009 involved no application of foliar fungicide, it will be seen that the Trigger product itself protected the plants. This is a substantial advantage inasmuch as the cost of repeated foliar fungicide applications was saved.

EXAMPLE 5

In this example, the saponins of the invention were tested for potato late blight control at Outlook, Sk. The test was conducted exactly as set forth in Example 2. However, late blight infection set in during the growing season. Data was then recorded on the top growth, and mechanical top killing on Aug. 10, 2000 destroyed the top growth. The tubers were left in the ground and harvested on Sep. 1, 2000, and further data recorded. The following Table 6 sets forth the important data.

Figure 4:
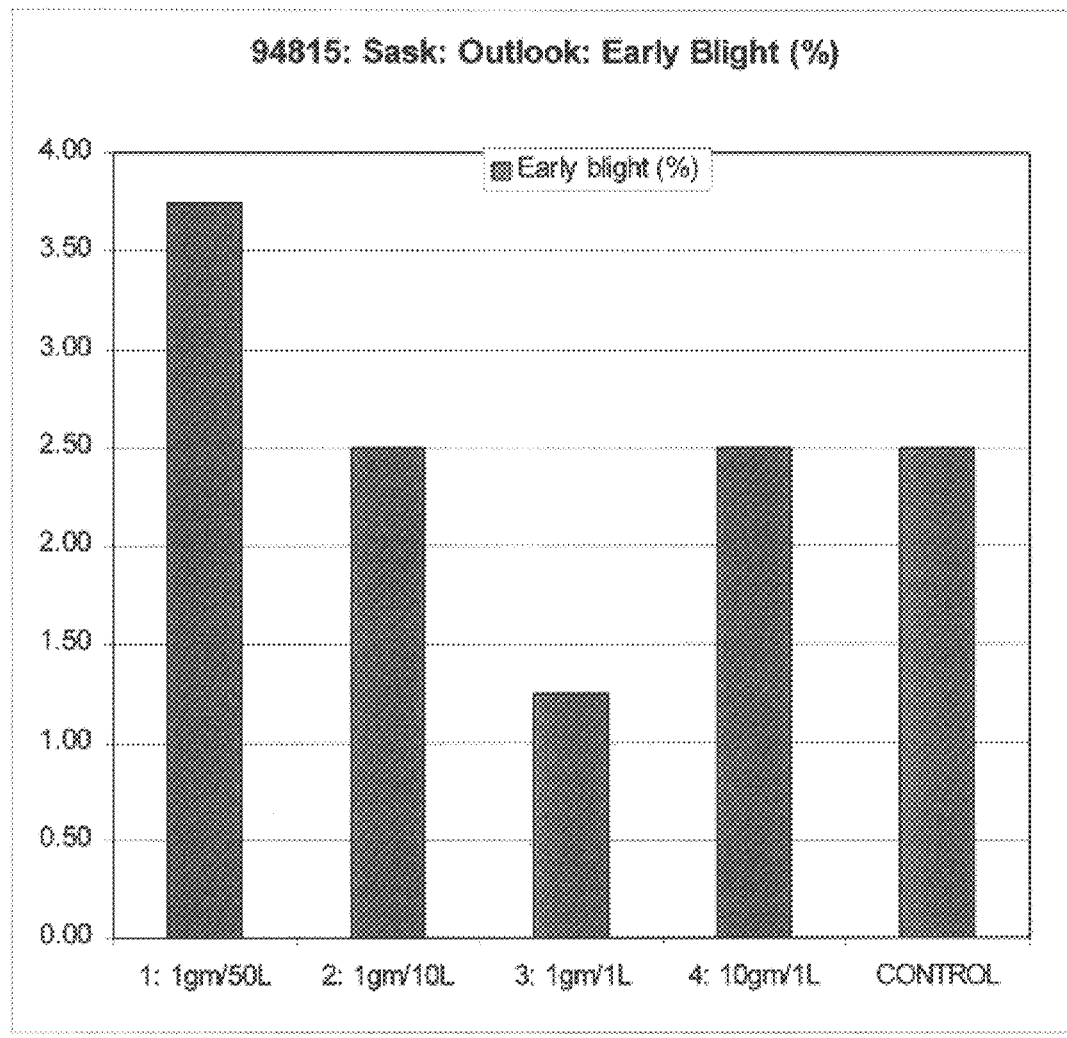
FIG. 4 is a graph illustrating the percent of early blight plants recorded in Example 5.
Figure 5:
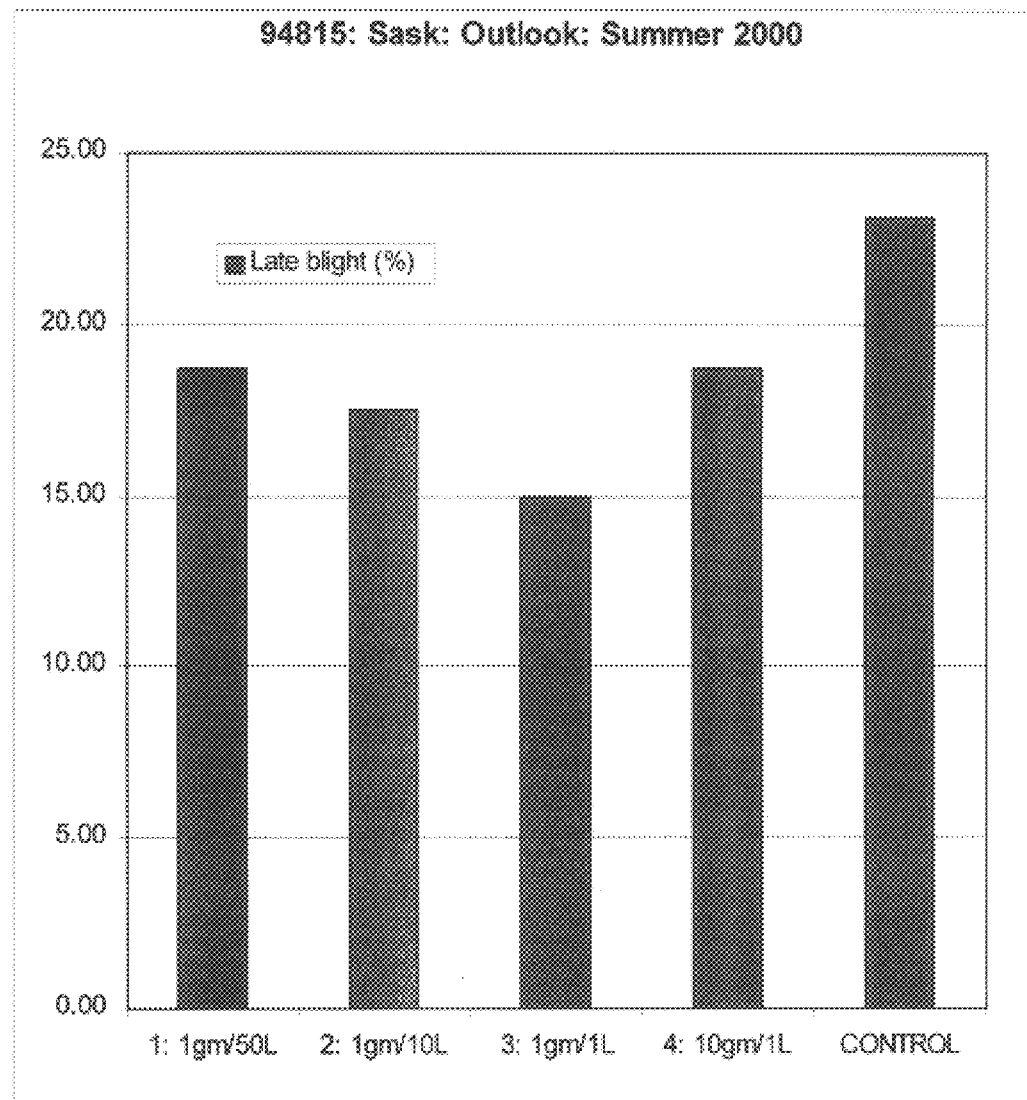
FIG. 5 is a graph of late blight plants recorded in Example 5.
Figure 6:
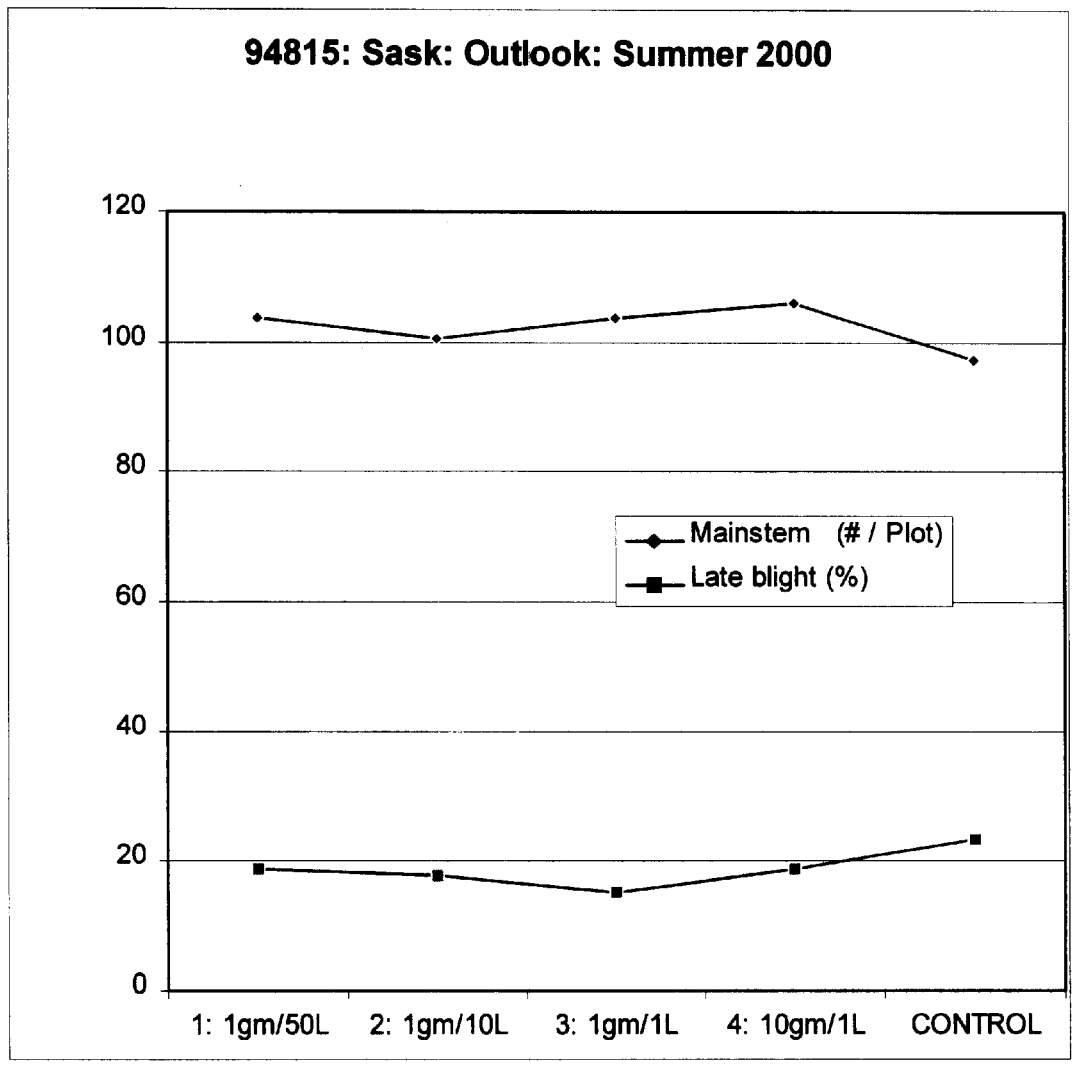
FIG. 6 is a graph illustrating the percent late blight and number of stems per tuber recorded in Example 5.

FIGS. 4–6 illustrate further the important data derived from this test.

TABLE 6

Data Averages: Average of Reps for Each Treatment - Outlook, Sk.

| Treatment # | Mainstem (#/Plot) | Late blight (%) | Early blight (%) | Black leg (# of Plants) | Canker (# of Plants) | Leaf roll (# of Plants) | Black scurf (%) |
|---|---|---|---|---|---|---|---|
| 1: 1 gm/50 L | 104 | 18.75 | 3.75 | 1 | 0 | 0 | 0.00 |
| 2: 1 gm/10 L | 101 | 17.50 | 2.50 | 0 | 0 | 0 | 0.00 |
| 3: 1 gm/1 L | 104 | 15.00 | 1.25 | 0 | 0 | 0 | 0.00 |
| 4: 10 gm/1 L | 106 | 18.75 | 2.50 | 0 | 0 | 0 | 0.00 |
| CONTROL | 98 | 23.13 | 2.50 | 1 | 0 | 0 | 0.00 |

The data: from this test also indicated that the treatment of the invention had an effect in controlling leaf roll virus.

EXAMPLE 6

In this example, the saponin products of the invention were used to treat elm trees infected with Dutch Elm disease. Six elm trees in Winnipeg, Minn. were discovered showing signs of Dutch Elm disease, ranging from 20–45% infected. The diseased trees were injected with a saponin dispersion (1 g saponin/L $H_2O$) prepared as described in Example 1. The application rate was 1 g of dry saponin/cm of trunk diameter at breast height. The dispersions were conventionally injected at the root flare, with the trees absorbing the dispersion within about 48 hours. The treated trees were monitored every day for approximately six weeks. The trees remained stable and exhibited no further wilt, flagging or leaf loss.

We claim:

1. In combination, a potato seed having an outer surface and a saponin composition applied to at least some of said outer surface, said outer surface having less than about 1 mg of aldehyde groups per square centimeter.

2. The combination of claim 1, wherein said saponin comprises a triterpene saponin.

3. A method of protecting plants or seeds, said method comprising contacting at least a portion of a potato seed with a protective amount of a composition consisting essentially of saponin so as to elicit a protective response in the seed.

4. A method of protecting plants or seeds, said method comprising contacting at least a portion of a potato plant with a protective amount of a composition consisting essentially of saponin so as to elicit a protective response in the plant, wherein said contacting step comprises applying said composition to a tuber of the plant.

5. A method of protecting plants or seeds, said method comprising contacting at least a portion of a plant or seed with a protective amount of a composition consisting essentially of saponin so as to elicit a protective response in the plant or seed, wherein said saponin is derived from a member selected from the group consisting of Quinoa and Quillaja.

6. A method of protecting plants or seeds, said method comprising contacting at least a portion of a potato seed with a protective amount of a composition consisting essentially of saponin so as to elicit a protective response in the seed, wherein said treated seed remains essentially free of symptoms of disease at least about 20 days after said contacting step.

7. A method of protecting plants or seeds, said method comprising contacting at least a portion of a plant or seed with a protective amount of a composition consisting essentially of saponin so as to elicit a protective response in the plant or seed, said composition being a particulate composition, said method including the step of blending the composition with a carrier prior to said contacting step, said carrier comprising talc.

8. A method of protecting plants or seeds from disease, said method comprising contacting a portion of a seed with a protective amount of saponin composition so as to elicit a protective response in the seed said portion having less than about 1 mg of aldehyde groups per square centimeter, and wherein said seed is a potato seed.

9. A method of protecting plants or seeds from disease, said method comprising contacting a portion of said plants or said seeds with a protective amount of saponin composition so as to elicit a protective response in the plant or seed, said portion having less than about 1 mg of aldehyde groups per square centimeter, wherein said contacting step comprises applying said composition to a tuber of the plant, and wherein said plant is a potato plant.

10. A method of protecting plants or seeds from disease, said method comprising contacting a portion of said plants or said seeds with a protective amount of saponin composition so as to elicit a protective response in said plants or said seeds, said portion having less than about 1 mg of aldehyde groups per square centimeter, wherein said saponin is derived from a member selected from the group consisting of Quinoa and Quillaja.

11. A method of protecting plants or seeds from disease, said method comprising contacting a portion of said plants or said seeds with a protective amount of saponin composition so as to elicit a protective response in the plant or seed, said portion having less than about 1 mg of aldehyde groups per square centimeter, wherein said treated plants or said treated seeds remains essentially free of symptoms of said disease at least about 20 days after said contacting step, wherein said saponin is derived from a member selected from the group consisting of Quinoa and Quillaja.

12. A method of protecting plants or seeds from disease, said method comprising contacting a portion of said plants or said seeds with a protective amount of saponin composition so as to elicit a protective response in said plants or said seeds, said portion having less than about 1 mg of aldehyde groups per square centimeter, said composition being a particulate composition comprising said saponin with a particulate carrier, said carrier comprising talc.

13. In combination, a potato seed having an outer surface and a composition consisting essentially of saponin, said composition being applied to at least some of said outer seed surface, wherein said saponin comprises a triterpenc saponin.

14. In combination, a potato seed having an outer surface and a composition consisting essentially of saponin, said composition being applied to at least some of said outer seed surface, wherein said saponin is derived from a member selected from the group consisting of Quinoa and Quillaja.

15. In combination, a potato seed having an outer surface and a composition consisting essentially of saponin, said composition being applied to at least some of said outer seed surface.

16. A method of protecting plants or seeds from disease, said method comprising contacting a portion of said plants or said seeds with a protective amount of saponin composition so as to elicit a protective response in said plants or said seeds, wherein said disease is selected from the group consisting of *Rhizoctonia solani, Helminthosporium solani, Phytophthora infestans*, Fusarium and viral diseases, and said portion having less than about 1 mg of aldehyde groups per square centimeter.

17. A method of protecting plants or seeds from disease, said method comprising contacting at least a portion of said plants or said seeds with a protective amount of a composition comprising saponin comprising a triterpene saponin, wherein said triterpene saponin comprises oleanolic acid, hederagenin, and phytolaccinic acid, so as to elicit a protective response in said plants or said seeds.

18. A method of protecting plants or seeds from disease, said method comprising contacting a portion of said plants or said seeds with a protective amount of saponin composition so as to elicit a protective response in said plants or said seeds and said portion having less than about 1 mg of aldehyde groups per square centimeter, said saponin comprising a triterpene saponin wherein said triterpene saponin comprises oleanolic acid, hederagenin, and phytolaccinic acid.

19. In combination, a plant or seed having an outer surface and a composition consisting essentially of saponin comprising a triterpene saponin, said composition being applied to at lest some of said outer plant or seed surface, wherein said saponin is derived from a plant. different than the plant or seed to which the composition is applied, said triterpene saponin comprising oleanolic acid, hederagenin, and phytolaccinic acid.

20. The method of claim 16, said viral disease being leaf roll virus.

* * * * *